US007678554B2

(12) United States Patent
Liu et al.

(10) Patent No.: US 7,678,554 B2
(45) Date of Patent: Mar. 16, 2010

(54) NUCLEIC ACID SHUFFLING

(75) Inventors: David R. Liu, Lexington, MA (US); Joshua A. Bittker, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 255 days.

(21) Appl. No.: 10/101,461

(22) Filed: Mar. 19, 2002

(65) Prior Publication Data

US 2003/0027180 A1 Feb. 6, 2003

Related U.S. Application Data

(60) Provisional application No. 60/277,015, filed on Mar. 19, 2001.

(51) Int. Cl.

*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl. .......................... 435/91.2; 435/6; 435/91.1; 536/23.1; 536/24.3; 536/24.33; 536/25.33

(58) Field of Classification Search ..................... 435/6, 435/69.1, 91.1, 91.2, 91.51, 183; 436/94, 436/501; 536/23.1, 24.3, 24.33, 25.3
See application file for complete search history.

(56) References Cited

U.S. PATENT DOCUMENTS

| | | | | |
|---|---|---|---|---|
| 5,723,323 | A | 3/1998 | Kauffman et al. | |
| 5,753,434 | A | 5/1998 | Ryner et al. | |
| 5,756,291 | A | 5/1998 | Griffin et al. | |
| 5,811,238 | A * | 9/1998 | Stemmer et al. | 435/6 |
| 5,830,721 | A | 11/1998 | Stemmer et al. | |
| 5,856,144 | A * | 1/1999 | Mierendorf et al. | 435/91.2 |
| 5,962,219 | A | 10/1999 | Gold et al. | |
| 6,066,457 | A * | 5/2000 | Hampson et al. | 435/6 |
| 6,110,900 | A | 8/2000 | Gold et al. | |
| 6,114,120 | A | 9/2000 | Jensen et al. | |
| 6,319,713 | B1 | 11/2001 | Patten et al. | |
| 6,319,714 | B1 * | 11/2001 | Crameri et al. | 435/440 |
| 6,352,842 | B1 | 3/2002 | Short et al. | |
| 6,569,435 | B1 | 5/2003 | Punnonen et al. | |
| 6,828,098 | B2 * | 12/2004 | Langmore et al. | 435/6 |
| 6,919,443 | B1 * | 7/2005 | Takahashi et al. | 536/24.2 |
| 7,135,310 | B2 | 11/2006 | Bradbury et al. | |
| 2001/0039014 | A1 * | 11/2001 | Bass et al. | 435/6 |
| 2003/0027180 | A1 | 2/2003 | Liu et al. | |

OTHER PUBLICATIONS

Luqmani et al., Subtraction hybridization cloning of RNA amplified from different cell populations microdissected from cryostat tissue section. Analytical Biochemistry, 222, 102-109, 1994.*

(Continued)

*Primary Examiner*—Frank W Lu
(74) *Attorney, Agent, or Firm*—Fish & Richardson P.C.

(57) ABSTRACT

Disclosed is a method of altering a nucleic acid. The method includes fragmenting a parent nucleic acid strand to generate nucleic acid fragments. At least a subset of the fragments are ligated to generate shuffled nucleic acid strands. A selected strand is identified from the shuffled nucleic acid strands for a criterion.

21 Claims, 2 Drawing Sheets pool of genomic or random starting DNA
DNase I / Mn++
blunt-ended DNA fragments
5-25 mol% hairpin adapter
T4 DNA ligase, 15% PEG
recombined DNA oligomers
digest with Sma I
ds DNA library
denature (pure water, 95 °C) or T7 RNA polymerase
ss DNA or RNA library
selection
1. bind to ligand-resin
2. elute with free ligand
selected DNAs or RNAs
PCR, cleave adapter

OTHER PUBLICATIONS

Webster's II New Riverside University Dictionary, p. 996.*

Breaker, DNA aptamers and DNA enzymes. Current opinion in chemical biology, 1, 26-31, 1997.*

Archemix website, printed 2002.

Dieckmann et al., "Mutant ATP-binding RNA Aptamers Reveal the Structural Basis for Ligand Binding", J. Mol. Biol. 273:467-478 (1997).

Ellington and Szostak, "In vitro selection of RNA molecules that bind specific ligands", *Nature* 346:818-822 (1990).

Ellington and Szostak, "Selection in vitro of single-stranded DNA molecules that fold into specific ligand-binding structures", *Nature* 355:850-852 (1992).

Famulok and Jenne, "Oligonucleotide libraries—*variatio delectat", Curr Opin Chem Biol*, 2:320-327 (1998).

Hermann and Patel, "Adaptive Recognition by Nucleic Acid Aptamers", *Science* 287:820-825 (2000).

Huizenga and Szostak, "A DNA Aptamer That Binds Adenosine and ATP", *Biochemistry* 34:656-665 (1995).

Jäschke et al., "In Vitro Selected Oligonucleotides as Tools in Organic Chemistry", *Synlett* 6:825-833 (1999).

Jhaveri et al, "In vitro selection of signaling aptamers", *Nature Biotechnology* 18:1293-1297 (2000).

Kolkman and Stemmer, "Directed evolution of proteins by exon shuffling", *Nature Biotechnology* 19:423-428 (2001).

Lorsch and Szostak, "In Vitro Selection of RNA Aptamers Specific for Cyanocobalamin", *Biochemistry* 33:973-982 (1994).

Lutz et al., "Creating multiple-crossover DNA libraries independent of sequence identity", *PNAS* 98:11248-11253 (2001).

Scott, "RNA catalysis", *Curr Opin Struct Biol*, 8:720-726 (1998).

Sen and Geyer, "DNA enzymes", *Curr Opin Chem Biol*, 2:680-687 (1998).

Sieber et al., "Libraries of hybrid proteins from distantly related sequences", *Nature Biotechnology* 19:456-460 (2001).

Stemmer, "Rapid evolution of a protein in vitro by DNA shuffling", *Nature* 370:389-391 (1994).

Tsuji et al., "Random multi-recombinant PCR for the construction of combinatorial protein libraries", *Nucleic Acids Research* vol. 29, No. 20, e97:1-10 (2001).

Wells, "A beginning, of sorts, for antisense", *Chemistry & Biology* 6:R49-R50 (1999).

Wilson et al., "Functional Requirements for Specific Ligand Recognition by a Biotin-Binding RNA Pseudoknot", *Biochemistry* 37:14410-14419 (1998).

Liu et al., "Engineering a tRNA and aminoacyl-tRNA synthetase for the site-specific incorporation of unnatural amino acids into proteins in vivo", *Proc. Natl. Acad. Sci. USA* 94:10092-10097 (1997)

Bogarad et al., "A hierarchical approach to protein molecular evolution," *Proc.Natl. Acad. Sci. USA*, 96: 2591-2595 (Mar. 1999).

Coco et al., "DNA shuffling method for generating highly recombined genes and evolved enzymes," *Nature Biotechnology*, 19: 354-359 (Apr. 2001).

Ostermeier et al., "A combinatorial approach to hybrid enzymes independent of DNA homology," *Nature Biotechnology*, 17(12): 1205-09 (1999).

Reidhaar-Olson et al., "Combinatorial cassette mutagenesis as a probe of the informational content of protein sequences," *Science*, 241(4861):53-7 (1988).

Bittker et al., "Directed Evolution of Protein Enzymes Using Nonhomologous Random Recombination," *PNAS*, 101: 7011-7016 (2004).

Bittker et al., "Nucleic Acid Evolution and Minimization by Nonhomologous Random Recombination," *Nature Biotechnology*, 20: 1024-1029 (2002).

Kawarasaki et al., "Enhanced Crossover SCRATCHY: Construction and High-Throughput Screening of a Combinatorial Library Containing Multiple Non-Homologous Crossovers," *Nucleic Acid Research*, 31:1-8 (2003).

Lutz et al., "Novel Methods for Directed Evolution of Enzymes: Quality, Not Quantity," *Current Opinion in Biotechnology*, 15: 291-297 (2004).

O'Maille et al., "Structure-Based Combinatorial Protein Engineering (SCOPE)," *J. Mol. Biol.*, 321: 677-691 (2002).

* cited by examiner

NUCLEIC ACID SHUFFLING

CROSS-REFERENCE TO RELATED APPLICATIONS

This application claims priority to U.S. Application Ser. No. 60/277,015, filed on Mar. 19, 2001, the contents of which is incorporated by reference in its entirety.

STATEMENT OF FEDERAL GOVERNMENTAL SUPPORT

This invention was made with government support under MCB-0094128 awarded by the National Science Foundation. The government has certain rights in the invention.

BACKGROUND

Proteins and nucleic acids employ only a small fraction of the functionality available to the modern chemist yet solve with ease chemical problems in binding, specificity, and catalysis that are well beyond the reach of current rational chemical design. These biopolymers can be diversified to generate numerous variants from which molecules with desired properties can be selected by Nature or by researchers in the laboratory. The sequence space of a 50 residue protein includes $10^{65}$ variants, while that of a 50 base oligonucleotide contains $10^{30}$ molecules.

In vitro molecular evolution efforts include diversification of a starting molecule into related variants from which desired molecules are chosen. Methods used to generate diversity in nucleic acid and protein libraries include whole genome mutagenesis (E. A. Hart et al. *Journal of the American Chemical Society* 1999, 121, 9887-9888.), random cassette mutagenesis (J. F. Reidhaar-Olson et al. *Methods Enzymol* 1991, 208, 564-86), error-prone PCR (R. C. Caldwell and G. F. Joyce. *PCR Methods Applic.* 1992, 2, 28-33), and DNA shuffling (Stemmer. *Nature* 1994, 370, 389-391). After diversification, biopolymers can be selected with novel or enhanced properties.

SUMMARY

The invention is based, in part, on the discovery that the random shuffling of fragments of a nucleic acid can provide a diverse pool of novel nucleic acids that include nucleic acids with new and/or enhanced properties.

In one aspect, the invention features a method that includes: a) fragmenting parent nucleic acid strands to generate three or more nucleic acid fragments from each parent nucleic acid strand; b) ligating at least a subset of the nucleic acid fragments to generate shuffled nucleic acid strands; and c) identifying a selected strand from the shuffled nucleic acid strands for a criterion, e.g., a non-coding property. Typically, the fragmenting and ligating are in vitro. The method can be used for altering nucleic acid sequences, e.g., for non-homologous shuffling of two or more parent nucleic acid strands.

In one embodiment, the parent nucleic acid strands are non-homologous and/or non-complementary. In another embodiment, the parent nucleic acid strands are less than about 90%, 80%, 70%, 60%, 50%, 40%, 30%, or 20% identical, on average. Of course, some strands may be at least partially homologous. In still another embodiment, the parent nucleic acid strands do not substantially anneal to one another at temperature below 55, 50, 45, 40, 35, or 30° C. under physiological conditions.

At least one of the shuffled nucleic acid strands, or at least 25, 50, or 75% of the strands include nucleic acid fragments from at least two of the parent nucleic acid strands. The nucleic acid fragments can have at least one terminus that can be ligated to at least one non-adjacent fragment. For example, the nucleic acid fragments can be double-stranded and can have at least one terminus that is a blunt end. Both termini can be blunt ends. The fragments can be less than about 2000, 1000, 700, 600, 500, 400, 300, 200, 100, or 50 nucleotides in length, and/or greater than about 10, 20, 40, 60, 80, 100, 200, or 500 nucleotides in length.

The median size of the shuffled nucleic acids can be less than about 2000, 1000, 700, 600, 500, 400, 300, 200, 100, or 50 nucleotides in length, and/or greater than about 10, 20, 40, 60, 80, 100, 200, or 500 nucleotides in length. In one embodiment, the method further includes isolating shuffled nucleic acid strands that are within a predetermined size range (e.g., the median size ranges above). The identifying includes identifying a selected strand from the isolated shuffled nucleic acid strands.

The number of different shuffled nucleic acids that are produced can be between $10^2$ and $10^{16}$, e.g., $10^4$ to $10^{16}$, $10^6$ to $10^{15}$, or $10^9$ to $10^{15}$.

The method can optionally include selecting some of the nucleic acid fragments from step a) for step b), e.g., size selecting the nucleic acid fragments, e.g., to remove the fragments less than 20, or 40 nucleotides in length, or greater than 700, 1000, or 2000 nucleotides in length, e.g., to obtain a pool of shuffled nucleic acid strands having a average length between 20 and 200, 20 and 400, 40 and 800, or 50 and 1200 nucleotides in length. The separation step can be a precipitation, electrophoretic separation, or chromatographic separation.

The ligation can be performed under conditions in which each fragment can be ligated to at least a non-adjacent fragment (i.e., not adjacent in the parent nucleic acid strand). The ligation can be performed such that the sequence and composition of the shuffled nucleic acid strands is random. The ligation can include a compound that increases the percentage of intermolecular ligation events. The compound can be a molecular crowding agent or an agent that increases the viscosity of the solution. Polyethylene glycol is an example of a compound with both properties.

The nucleic acid can be RNA, single-stranded DNA, or double stranded DNA.

The selected strand can be a copy (e.g., a cloned copy or amplified copy) of or a transcribed or reverse-transcribed copy of a shuffled nucleic acid strand. The parent nucleic acid strands can be fragmented in the same container or in different containers and then combined. The parent nucleic acid strands can be fragmented, for example, with a non-site specific agent such as a nonspecific endonuclease (e.g., DNaseI), a restriction enzyme (e.g., a a Type II enzyme, four-base cutter, a Type IIS enzyme), a chemical reagent (e.g., a hydroxyl radical generator such as Fe(II)-EDTA-hydrogen peroxide), or a physical method (such as sonication or shearing).

The method can further include one or more of the following: ligating a hairpin oligonucleotide to at least a subset of the shuffled nucleic acid strands; cleaving the shuffled nucleic acid strands with a endonuclease (e.g., a Type II restriction enzyme, or a Type IIS restriction enzyme) which cleaves in the hairpin oligonucleotide or in the shuffled nucleic acid strands; and amplifying the shuffled nucleic acid strands with a primer, e.g., a primer which anneals to a sequence in the hairpin oligonucleotide. The hairpin oligonucleotide can include a sequence that is a promoter of RNA transcription, e.g., a T7 polymerase promoter, or a transcription terminator.

The method can further include ligating a synthetic oligonucleotide, e.g., to at least one fragment. The synthetic oligonucleotide can include, for example, a random sequence; a aptamer features such as a tetraloop, a bulge, or a hairpin; or a sequence encoding a patterned peptide. The synthetic oligonucleotide can be spiked into the ligation at a variety of molar ratios, e.g., between 0.001 and 0.2 or 0.01 and 0.05. A plurality of different synthetic oligonucleotides, e.g., in duplex form, can be added.

The criterion for selection can be a physical criterion (e.g., size, conformation, or structural stability) or a functional criterion (e.g., ability to bind a ligand, ability to catalyze an reaction, or ability to modulate a process). The selection step can include contacting the shuffled nucleic acid strands to a ligand, e.g., a ligand attached to a solid support, and selecting one or more strands that bind the ligand. The selection step can include a wash, e.g., multiple washes of increasing stringency, or a wash with a competing compound, e.g., a compound known to bind the ligand. The ligand can be a polypeptide or a small molecule ligand, or generally any molecule that can be immobilized or differentiated. The term “small organic molecule” refers to an organic compound with a molecular weight of less than 3000 Daltons. For example, the small molecule ligand can be a transition state analogue.

The method can further include identifying a second selected strand for the criterion from the shuffled nucleic acid strands, and repeating steps a), b), and c) parent nucleic acids that include the selected strand and the second selected strand. The method can also further include amplifying the shuffled nucleic acid strands, e.g., using a primer that anneals to the hairpin oligonucleotide to produce amplified shuffled nucleic acid strands; denaturing the amplified shuffled nucleic acid strands to form a first and a second nucleic acid strand; and cooling the first and second nucleic acid strand such that the first strand does not form a nucleic acid duplex with the second strand and such that the termini of the first strand anneal one another to form an intramolecular duplex.

The identifying can include synthesizing a nucleic acid aptamer in a cell and evaluating a property of the cell, e.g., ability to divide, respond to a stimulus, transcription profile, and so forth.

In a related aspect, the invention features a method that includes: a) fragmenting a parent nucleic acid strand to generate three or more nucleic acid fragments; b) ligating at least a subset of the nucleic acid fragments at random to generate shuffled nucleic acid strands, at least one of the shuffled nucleic acid strands includes one or more of: reordered nucleic acid fragments from the parent nucleic acid strand, a repeated nucleic acid fragment from the parent nucleic acid strand, or a deletion of a nucleic acid fragment; and c) identifying a selected strand for a non-coding property from the shuffled nucleic acid strands. Embodiments of this method can include features described above or elsewhere herein.

In another aspect, the invention features a method of altering a nucleic acid. The method includes fragmenting (e.g., at random) a parent nucleic acid strand to generate three or more nucleic acid fragments, each nucleic acid fragment having a terminus that can be ligated to at least one non-adjacent fragment; ligating a hairpin nucleic acid and at least a subset of the nucleic acid fragments to generate shuffled nucleic acid strands, each shuffled nucleic acid strand including at least one inserted, deleted, or rearranged nucleic acid fragment relative to the parent nucleic acid strand; amplifying the shuffled nucleic acid strands using a primer that anneals to the hairpin nucleic acid; selecting a strand from the amplified shuffled nucleic acid strands for a criterion. Embodiments of the method are described herein, e.g., as for the method above.

In still another aspect, the invention features a method of altering a polypeptide. The method includes: providing a parent nucleic acid strand encoding a parent polypeptide; fragmenting the parent nucleic acid strand to generate three or more nucleic acid fragments, each nucleic acid fragment having a terminus that can be ligated to at least one non-adjacent fragment; ligating at least a subset of the nucleic acid fragments to generate a shuffled nucleic acid strand, wherein the shuffled nucleic acid strand has at least one nucleic acid fragment inserted, deleted, or rearranged; and expressing a shuffled polypeptide encoded by the shuffled nucleic acid strand. The fragmenting can be such that (a) the parent nucleic acid strand is fragmented by a non-site specific agent (e.g., a non-specific endonuclease), and/or (b) the average size of the fragments is less than 2000 nucleotides. The shuffled polypeptide can be attached to the shuffled nucleic acid strand, e.g., using a covalent bond, a filamentous phage display system, or a cell. The shuffled nucleic acid strand can include a nucleic acid fragment from a second parent nucleic acid strand encoding a second polypeptide. For example, the second parent nucleic acid strand can be less than 70% identical to the parent nucleic acid strand. Embodiments of the method are described herein.

In another aspect, the invention features a kit of shuffled nucleic acid strands. The kit includes a plurality of nucleic acid strands, e.g., at least 5, 10, 20, 50, 100, 200, 500, 1000, or 2000 strands. Each nucleic acid strand can include at least three, four, five, six, or ten reference fragments or their complements. The reference fragments are the same for each strand of the plurality, or at least three, four, five, six, or ten of the strands are the same for the each strand of the plurality. Each strand of the plurality is unique among the plurality with respect to the order and orientation of the reference fragments. The nucleic acid strands can be disposed in the same container, or in different containers. In one embodiment, the nucleic acid strands are aptamers.

In still another aspect, the invention features kit that includes an endonuclease such as a non-specific endonuclease; a ligase; a hairpin oligonucleotide; and, optionally, instructions for fragmenting a parent nucleic acid strand with the endonuclease to generate nucleic acid fragments, and ligating the hairpin oligonucleotide and the fragments using the ligase to generate shuffled nucleic acid strands. The kit can also include a primer that anneals to a self-complementary region of the hairpin oligonucleotide.

The term “non-homologous” refers to two nucleic acid sequences having sufficient number of differences that the two sequences are unable to recombine with each other in a standard host cell, particularly in an *E. coli* cell. The term “in vitro non-homologous” refers to two nucleic acid sequences having sufficient number of differences that the two sequences are unable to recombine using an in vitro recombination method such as the recombination method generally described in Stemmer. *Nature* 1994, 370, 389-391.

The term “shuffled” refers to a polymer having at least one fragment rearranged, reoriented, inserted, or deleted with respect to an appropriate reference polymer, e.g., a parent polymer.

The term “random” refers to condition wherein events are determined by a probability distribution. The distribution may include a bias, e.g., dependent on the relative concentrations of starting material. For example, in one embodiment, the parental nucleic acid strands may include a biased amount of one species relative to another. The ligation of a mixture of fragments generated from such a pool of starting material can nevertheless be random.

The term "oligonucleotide," as used herein refers to a nucleic acid polymer of about 5 to 140 nucleotides in length.

The term nucleic acid "aptamer," as used herein, refers to a nucleic acid molecule which has a conformation that includes an internal non-duplex nucleic acid structure of at least 5 nucleotides. For example, an aptamer can be a single-stranded nucleic acid molecule which has regions of self-complementarity. For another example, an aptamer can be nucleic acid molecule which binds a ligand other than a nucleic acid.

A "hairpin nucleic acid," "hairpin oligonucleotide," or "hairpin" refers to a nucleic acid that includes a first, second, and third region such that the first region is complementary, (e.g., 95%, 99%, or 100%) complementary to the third region, and the second region is complementary not neither the first nor the third region.

The term "binds," and "binding" refer to a physical interaction for which the apparent dissociation constant of two molecules is at least 0.1 mM. Binding affinities can be less than about 10 μM, 1 μM, 100 nM, 10 nM, 1 nM, 100 pM, 10 pM, and so forth. The term "ligand" refers to a compound which can be specifically and stably bound by a molecule of interest.

The term "non-coding property" refers to a property of a nucleic acid molecule that is not a mere function of a protein that it may (or may not) encode. Examples of non-coding properties include specific binding and catalysis.

In the case of proteins and nucleic acids, the sequence space of even small peptides or oligonucleotides is far larger than the number of variants that can be created and sampled by researchers. The identification of useful molecules from even a miniscule fraction of this space would be greatly enhanced by the use of laboratory approaches that intelligently focus on identifying diversified and enriched variants of sequences of interests. Such diversified sequences are frequently nearby in sequence space.

The sequence space of nucleic acid sequences includes nucleic acid aptamers. These molecules can be used in a variety of scenarios, including diagnostic and therapeutic medical uses. For example nucleic acid aptamers can be isolated that are inhibitors of human polypeptide such as thrombin. Nucleic acids can also be isolated that cleave target RNAs relevant to human disease. Further nucleic acid aptamer can be delivered into the intracellular environment, e.g., by a virus, where the cellular machinery can propagate or transcribe it in a regulated manner. Other aptamers can be used as biosensors for diagnostic purposes.

The details of one or more embodiments of the invention are set forth in the accompanying drawings and the description below. Other features, objects, and advantages of the invention will be apparent from the description and drawings, and from the claims.

DETAILED DESCRIPTION

The invention provides shuffled nucleic acid sequence by ligation of nucleic acid fragments obtained from parent strands, such as non-homologous parent strands. The method is referred to as the nucleic acid shuffling method (and also as "Non-homologous Random Recombination" or "NRR"). The method does not require homology between the parental strands for recombination. However, at least in some cases, such homology may be present.

Figure 1:
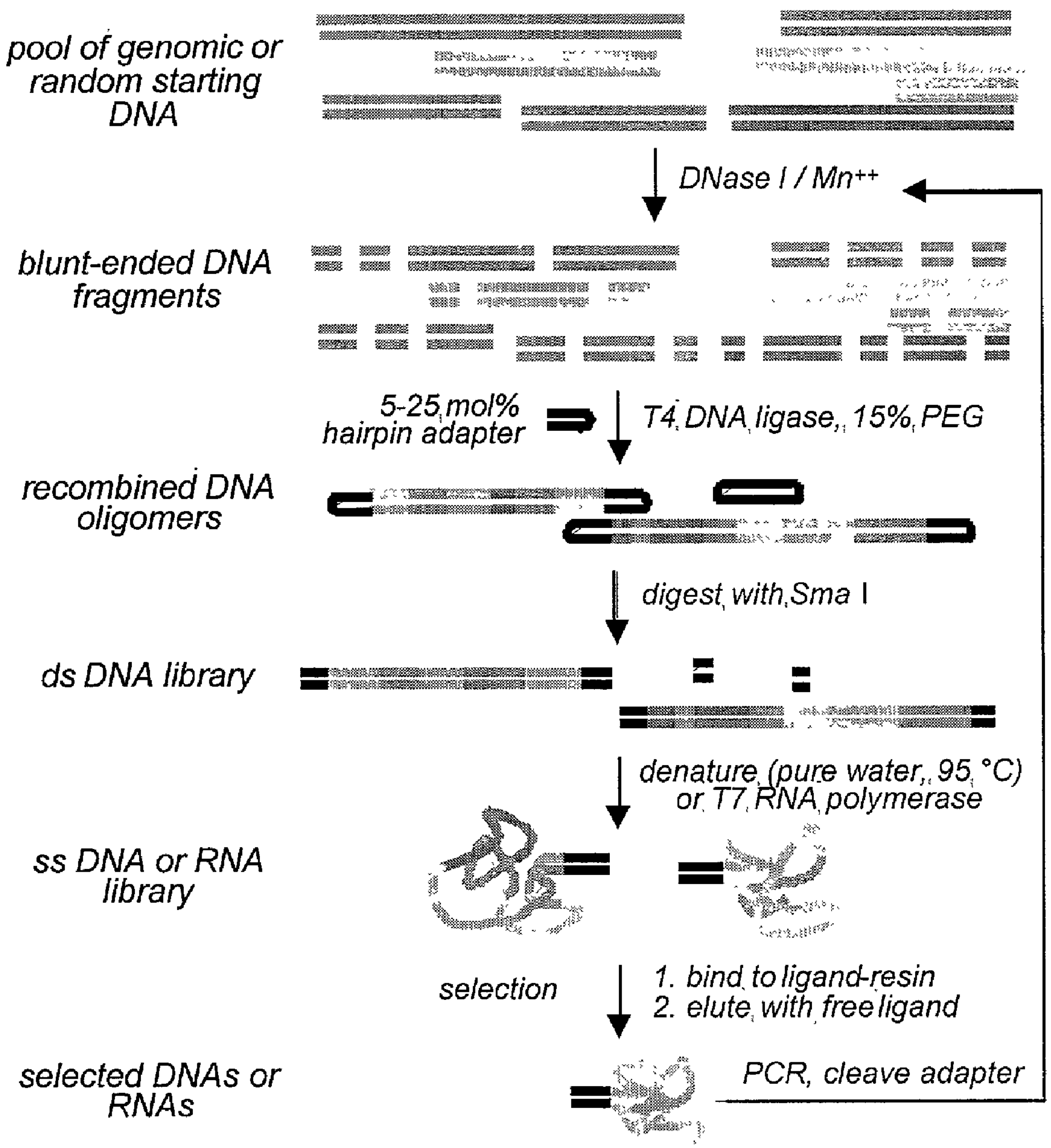
FIG. 1 is a schematic of an example of the nucleic acid shuffling method.

Referring to the example in FIG. 1, a pool of genomic DNA or random starting DNA is randomly digested with DNaseI in the presence of manganese. The DNase I digestion of these parent nucleic acid strands generates 5'-phosphorylated DNA fragments of approximately 10-100 bp in length. The average length of the fragments used for shuffling is monitored and controlled by regulating the DNase I digestion conditions, e.g., temperature, enzyme concentration, substrate concentration and divalent cation concentration. The fragmenting reaction is terminated and the fragments separated from the inactivated DNaseI. These fragments are enzymatically transformed into blunt-ended double strands of DNA by reaction with T4 DNA polymerase, which catalyzes both the extension of 5' overhangs and the exonucleolytic cleavage of 3' overhangs to leave 5' phosphates (Campbell and Jackson. *J. Biol. Chem.* 1980, 255, 3726-3725.). Klenow DNA polymerase can also be used, e.g., if the fragmenting method does not generate 3' overhangs. The polymerase reaction is terminated, and the blunted fragments are purified from the reaction mixture. The blunted fragments are then randomly ligated together using T4 DNA ligase, which catalyzes the efficient ligation of blunt-ended DNA independent of sequence. The ligation reaction includes 15% polyethylene glycol (PEG), e.g., of average molecular weight about 4000 to 8000 Daltons. PEG was observed to increase the frequency of intermolecular ligation events as described below.

DNA hairpins can also be included in the ligation reaction to control the average length of the ligated shuffled nucleic acid strand library and to ensure that all library members are flanked by defined sequences suitable for PCR or subcloning. One or more DNA hairpins of defined sequence are added to these intermolecular ligation reactions, e.g., prior to or after addition of DNA ligase. The terminus of DNA molecule capped by ligation to a hairpin can no longer ligate to other molecules. The DNA hairpins can be included at any concentration, for example, at a molar concentration of 0.0001% to 100%, 0.1% to 90%, 1% to 50%, or 2% to 25% of the molar concentration of the nucleic acid fragments. Higher concentrations of a DNA hairpin tends to lowers the average molecular weight of the shuffled nucleic acids, whereas a reduced concentrations of a DNA hairpin tends to yield shuffled nucleic acids with longer average lengths. The user can, therefore, regulate the length of the produced shuffled nucleic acid strand. Control of this parameter, for example, allows the evolution of nucleic acids that are minimized relative to parental nucleic acids or that are expanded relative to parental nucleic acids.

The process can include digesting the ligation reaction with a restriction enzyme that cleaves the ends of each hairpin, and subjecting the resulting double-stranded material to the polymerase chain reaction (PCR) using a primer complementary in sequence to a sequence in the hairpin. The PCR conditions, e.g., error-prone PCR conditions, can be chosen to reduce polymerase fidelity to introduce additional mutations, particularly substitutions. The primer binding site can be in the self-complementary region of the hairpin.

In one embodiment, two different hairpin nucleic acids are added. In another embodiment, a single hairpin nucleic acid is added, e.g., to one or both termini.

A shuffled nucleic acid can be amplified by a variety of methods in addition to PCR (U.S. Pat. No. 4,683,196 and 4,683,202). Such other methods include rolling circle amplification ("RCA," U.S. Pat. No. 5,714,320), isothermal RNA amplification or NASBA, and strand displacement amplification (U.S. Pat. No. 5,455,166).

Aptamer Formation

The formation of nucleic acid aptamers from double stranded DNA is facilitated by the use of a single hairpin nucleic acid. Because one end of each individual PCR product is complementary to its other end in this embodiment, denaturation of the products can results in the formation of a monomeric single-stranded DNAs that is stabilized by a duplex region formed by the annealed ends. For example, the amplified double stranded DNA can be purified and resuspended in pure water, denatured at 95° C. and cooled rapidly in order to favor aptamer formation over duplex formation.

Additional methods are available for efficient aptamer formation. For example, the amplification primer (e.g., primer annealing to the ligated hairpin) can include a moiety for attachment to a solid support. Amplification products can be bound, e.g., by oxidation of a thiol or a non-covalent linkage such as biotin-avidin, to a solid support, e.g., a planar surface, a matrix, or a bead, at a concentration that only one strand of the amplification product can be stably attached. Denaturation of bound amplification products (e.g., separates the strands of each duplex amplification product from unbound strand which can be removed by a wash). Renaturation of bound strands produces in monomeric nucleic acid aptamers.

In another example, RNA copies of the shuffled nucleic acid strand are produced, e.g., using a T7 polymerase promoter that can be attached to the shuffled nucleic acid, e.g., by ligation. The RNA copies can be used as aptamers themselves, or can be reverse transcribed to produce DNA aptamers and then the RNA templates removed using a ribonuclease. Structural features of nucleic acid aptamers formed from shuffled nucleic acid can include variously positioned regions of self-complementarity. These features can stabilize the folded conformation of an aptamer. Since the random ligation can result in the inclusion of two copies of a fragment of a parent strand, one copy in each orientation, an aptamer formed from a single strand of the shuffled nucleic acid can include the nucleic acid fragment and its complement. This internal complementarity can promote the formation of secondary structures. These secondary structures are known to be critical to the binding and catalytic abilities of nucleic acids, e.g., by offsetting some of the entropic cost of intramolecular folding (Hermann and Patel. *Science* 2000, 287, 820-5; Scott. *Curr Opin Struct Biol* 1998, 8, 720-6; Sen and Geyer. *Curr Opin Chem Biol* 1998, 2, 680-7.). Libraries of nonhomologously recombined, single-stranded DNAs formed in this fashion are ready for in vitro selection.

In another implementation, the ligation step of the method is further enriched by the inclusion of synthetic double-stranded nucleic acids that include sequence features useful for aptamer functionality. Such sequences include sequences which as single-stranded nucleic acids would form tetraloops, bulges, or hairpins. By including such sequences during the ligation phase, these features are interspersed with fragments from the parental nucleic acids.

Screening Aptamers

Aptamers are easily screened as untagged molecules in vitro since a selected aptamer can be recovered by standard nucleic acid amplification procedures. The method can be enhanced, e.g., in later rounds of selection, by splitting selected aptamers into pools and modifying each aptamer in the pool with a detectable label such as a fluorophore. Pools having aptamers that functionally alter the properties of the label can be identified. Such pools can be repeatedly split and reanalyzed to identify the individual aptamers with the desired properties (see, e.g., Jhaveri et al. *Nature Biotechnol.* 18:1293).

In addition, aptamers can be screened for activity in vivo. For example, shuffled nucleic acids can be cloned into an expression vector that is introduced into cells. RNA aptamers resulting from the expressed shuffled nucleic acids can be screened for a biological activity. Cells having the activity can be isolated and the expression vector for the selected RNA aptamer recovered.

Non-specific Nucleic Acid Cleavage

A variety of methods can be used to fragment parent nucleic acid strands for the nucleic acid shuffling method described here.

As described above, the parent strands can be digested at random location by an enzyme or a chemical reagent. For example, the chemical reagent can be o-phenanthroline-copper or a hydroxyl radical generator such as Fe(II)-EDTA-hydrogen peroxide. The enzyme can be an endonuclease, such as DNaseI, or an exonuclease. In some implementations, the parent nucleic acid coiled around nucleosomes or another structure to facilitate the digestion (e.g., by DNaseI) of the parent nucleic acid into fragments of regular size, e.g., a length of about 70 to 120 nucleotides.

In another implementation, the parent strands are digested at frequent non-random locations, e.g., using one or more site-specific restriction enzymes such as a 4-base pair cutter, a 6-base cutters, or a pool of such enzymes.

The parent nucleic acid strand can be random synthetic nucleic acid, genomic nucleic acid, a gene or sequence of interest, or a pool of such sequences. For example, a pool of sequence can be a collection of sequence obtained from a previous round of shuffling and selection.

Polypeptides

The method described here can be used to shuffle polypeptide sequences. A nucleic acid strand encoding a polypeptide is used as the parent sequence. The coding strand is fragmented as described, and the fragments are relegated to form a library of shuffled nucleic acid coding sequences. Although a significant fraction of such sequences may contain in-frame stop codons, within a large library a reasonable proportion of sequence still include a substantial polypeptide coding region. For each ligation of two segments, only one of six products is expected to contain an in-frame ligation of the two segments. A library of $10^{10}$ shuffled sequence that include five fragments still includes about $10^6$ in-frame shuffled coding sequences. Such a population is a substantial pool from which to identify diversified sequences. Moreover, the size of the fragments used for constructing shuffled polypeptide coding nucleic acids can be at least approximately 200, 300, 400, 500, 600, 700, 800, 1000, 1200 or 1400 nucleotides.

The shuffling of coding nucleic acid sequences can also be enriched by the inclusion of synthetic sequences such as randomized amino acid sequences, patterned amino acid sequence, computer-designed amino acid sequences, and combinations of the above. Particularly useful are synthetic sequences that encode peptides with functional properties or with particular structural propensities. For example, β-strands can be encoded by a degenerate oligonucleotide in which codons for hydrophobic residues, e.g., codons [GAC]-[T]-[N], are alternated with codons for hydrophilic residue, e.g., codons [GTC]-[A]-[N], from a degenerate can encode artificial amino acid sequences. Similarly amphipathic α-helices can be patterned based on the helical pitch of the canonical α-helix. Cho et al. (2000) *J Mol Biol* 297:309-19, for example, describes methods for preparing libraries of randomized and patterned amino acid sequences. Other functional sequence which can be included are sequences which encode cysteine, serine, and/or histidines; and sequences found in a database of motifs, e.g., ProSite.

In one particular embodiment of polypeptide shuffling, the parental coding nucleic acids are not fragmented randomly. Rather, individual structural domains are amplified from the parental coding nucleic acids, e.g., amplifying multiple signal transduction modules from eukaryotic cDNA using a large number of specific primers. The primers are designed such that all the domains are in the same frame. The amplified fragments are then ligated together randomly to generate shuffled coding nucleic acids. The library of shuffled nucleic acid can be screened (see below), e.g., in cells for novel signal transduction circuits.

The method can, for example, be used to screen for polypeptide variants with higher thermal stability. Such variants can be generated in a number of ways. One possibility is the duplication and/or rearrangement of a structural feature induces domain-swapping and oligomerization of the polypeptide. Such evolutionary events may also have occurred under natural conditions (Bennett et al. *Protein Sci.* 1995:2455-68).

To determine the "percent identity" of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes) using the Needleman and Wunsch ((1970) *J. Mol. Biol.* 48:444-453) algorithm which has been incorporated into the GAP program in the GCG software package, using a Blossum 62 scoring matrix, a gap penalty of 12, a gap extend penalty of 4, and a frameshift gap penalty of 5. The percentage of identical nucleotides is determined from the optimal alignment. The shuffled nucleic acid coding regions can be used to express shuffled polypeptides that are displayed as RNA fusions (Roberts and Szostak *Proc Natl Acad Sci U S A.* 1997 94:12297-302; PCT WO 98/31700), on chips (PCT WO 99/51773), on bacteria (Ladner, U.S. Pat. No. 5,223,409), on spores (Ladner U.S. Pat. No. 5,223,409), on plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.). The displayed polypeptide can be selected for functional properties, e.g., for binding to a ligand such as a target molecule or a transition state analog.

The shuffled nucleic acid coding regions can also be used to express shuffled polypeptides in cells. The cells can have an altered genetic composition, e.g., in order to provide a selective environment suitable for identifying expressed polypeptides having a particular activity (see Joo et al. *Nature* 1999; 399:670-3 e.g., for an example of a catalytic selection using a genetically modified host cell ).

The shuffled nucleic acid coding regions can be inserted into a two-hybrid vector, e.g., so that the expressed shuffled polypeptide is fused to a nucleic acid binding domain or to a transcriptional activation domain (see, e.g., U.S. Pat. No. 5,283,317). The vector with the cloned shuffled coding region can be inserted into a cell have a corresponding two-hybrid vector expressing a target polypeptide. Shuffled polypeptides which bind the target polypeptide activate transcription and can be readily identified for characterization and additional rounds of selection.

Sequence Minimization

The nucleic acid shuffling method can be used to minimize a biological sequence, e.g., for characterization to identify essential features. The essential features can be adapted for use in engineered sequences. For example, the method can be used to minimize a nucleic acid aptamer or a polypeptide by minimizing the coding nucleic acid.

One additional example is the minimization of transcriptional regulatory regions. Regulatory genomic DNA is fragmented and relegated using the shuffling method described here. The shuffled nucleic acid strands are cloned upstream of a promoter in a eukaryotic expression vector having a reporter gene such as green fluorescent protein operably linked to the promoter and upstream regulatory sequences. These reporter vectors bearing the cloned shuffled nucleic acid are transformed into host cells. Individual transformants are analyzed for activation or repression of the reporter gene under the desired condition, e.g., exposure to a therapeutic drug, a hormone, a cytokine, and so forth. Transformants with desired properties are isolated, and the shuffled nucleic acid is sequenced and characterized. The shuffled nucleic acid can be used to generate expression vectors that are triggered by the desired conditions. Such constructs are particularly useful for the design of novel genetic circuits (see, e.g., Gardner et al. (2000) *Nature* 402:339; and Becskel & Serrano et al. (2000) *Nature* 405:590).

Sequence Enrichment

The nucleic acid shuffling method described here can be used to enhance a biological sequence, e.g., to provide additional features which confer additional or new properties, e.g., increased stability, regulation by an allosteric effector, increased affinity or enzymatic properties. For example, the method can be used breed a hybrid nucleic acid aptamer from two parent nucleic acid aptamers with different properties. Hybrid nucleic acid aptamers can be identified, for example which catalyze a reaction similar to one parent, but are also allosterically regulated by a ligand bound by another parent.

Sequence Analysis

The methods described herein can be coupled with sequence analysis. For example, if multiple evolved clones are selected, they can be compared to identify a segment that recurs among the clones. Such segments may represent functional or structural motifs useful for the selected property. Similarly, if a single sequence is minimized, the reoccurrence of a segment can also be indicative of its functional or structural importance. The methods can include inferring from a plurality of clones selected for a criterion, one or more valued segments. Rational design can be used to produce small nucleic acids that include the valued segments. In another embodiment, the valued segments are inserted into another shuffling reaction, e.g., to evolve a multi-functional nucleic acid sequence.

The program MACAW (Multiple Alignment Construction and Analysis Workbench), available from the National Center for Biotechnology Information (Bethesda Md., USA) can be used to compare selected clones and identify a recurring segment.

Without further elaboration, it is believed that the above description has adequately enabled the present invention. The following examples are, therefore to be construed as merely illustrative, and not limitative of the remainder of the disclosure in any way whatsoever. All publications cited herein are hereby incorporated by reference in their entirety.

EXAMPLE

Shuffled Library Construction

The steps of the method for non-homologous recombination were successfully executed and analyzed. Two shuffled nucleic acid libraries were produced.

Library A. This library is a library of shuffled human genomic sequences. Human genomic DNA was digest with DNase I in the presence of divalent magnesium. Human genomic DNA was selected, in part, for its increased secondary structure content relative to purely random DNA. Size selection of the fragments was achieved by modulating the duration of the digestion followed by gel purification. Conditions were selected such that the average fragment size ranged from 10 to 100 bp as required. The fragments were then treated with T4 DNA polymerase, which generates blunt ends by filling in 5' overhangs and degrading 3' overhangs.

Library B. This library is a library of shuffled random synthetic sequences. Random 40-mer oligonucleotides were synthesized and enzymatically 5'-phosphorylated with T4 polynucleotidyl kinase. The oligonucleotides were treated with T4 DNA polymerase which extended annealed and partially annealed oligonucleotides into double stranded DNA.

Both libraries were prepared as follows. Treatment of the blunt-ended fragment pool with T4 DNA ligase to effect nonhomologous recombination resulted in an increase in the average molecular weight of approximately a factor of two. This extent of ligation may result from intramolecular ligation events that are prematurely terminating such as end joining and circular dead-end products of approximately 100-200 bp.

More extensive nucleic acid shuffling was achieved by modification of the ligation conditions. Polyethylene glycol (PEG) was added to the fragment ligation reactions in order to increase the frequency of intermolecular ligations. At a final concentration of 15% PEG, the nearly exclusive intermolecular ligation of the blunt ended DNA fragments was observed, unexpectedly generating products more than 10,000 bp in length.

DNA hairpins were designed to terminate the ligation process and install defined sequences on the ends of the library members. Two versions of this hairpin are formed by the exemplary sequences listed as follows:

5 '-GGGAATTCTAGAAGCTTCCCGGGGGGC-CCGCGCGGGCCCCCCGGGAAGCTTC TAGAAT-TCCC-3' (SEQ ID NO: 1)

The above hairpin includes sites for EcoRI, HindIII, XbaI, and SmaI.

5'-GGGTCCGGATACGAATTCCCCGGGGGC-CCGCGCGGGCCCCCGGGGAATTCGT ATCCG-GACCC-3' (SEQ ID NO:2)

The above hairpin includes sites for BspE1, BciVI, EcoRI, and SmaI.

The second version of the hairpin (SEQ ID NO:2) can be removed in a "scarless" manner from the library by digestion with the Type IIS restriction enzyme, BciVI digestion, followed by treatment with T4 DNA polymerase. The Type IIS recognition site is located such that cleavage precisely removes the hairpin precisely from the shuffled nucleic acid strands. The other version of the hairpin (SEQ ID NO: 1) does not include a Type IIS restriction site Both hairpin sequences included a variety of Type II restriction sites in their self-complementary regions. For example, the exemplary hairpins above included several restriction endonuclease sites flanked on the closed end by a SmaI cleavage site and on the open end by half of a SmaI site. Hairpin dimers formed during the ligation process are conveniently destroyed by digestion with SmaI. Such digestion avoids forming undesired products during subsequent PCR steps. Other restriction enzymes were used for cloning and mapping.

Addition of 2-25 mol % of these adapter hairpins to the PEG-promoted intermolecular ligation reactions terminated the ligation events. The average length of the ligation products was inversely dependent on the concentration of adapters, consistent with their proposed role in terminating end joining. This feature enables the selection application of evolutionary pressure for minimizing or extending the length of a functional nucleic acid. Digestion of this material with SmaI removed the closed ends of each library member facilitating denaturation during PCR and also destroyed undesired hairpin dimers, i.e., hairpin oligonucleotides that ligate to each other without including any shuffled nucleic acids.

PCR of the resulting recombined, double-stranded DNA using a single 21-base primer matching one arm of the adapter hairpin (the "adapter primer") produced a product pool. The average size of the pool related to the ratio of hairpin DNA included in the ligation (e.g., in one case ~200 bp). The shuffled nucleic acid with ligated hairpins at both ends could also be successfully amplified using error prone PCR.

The amplified double-stranded shuffled nucleic acids were then denatured to form individual DNA aptamers, each aptamer formed from a single nucleic acid strand. A variety of conditions using low salt concentrations, metal chelators, and hydroxide were tested for their ability to efficiently melt the double stranded products into single strands. It was found that simple heating at 94° C. in very pure water followed by rapid cooling and addition of desired buffer afforded the most reproducible and high yielding DNA aptamer formation. These conditions favored the folding of aptamers over the renaturation of double-stranded DNA. Aptamers were distinguished from canonical double-stranded DNA by their decreased molecular weight as assayed by agarose gel electrophoresis.

Aptamer generation under these conditions to the PCR amplified shuffled nucleic acid libraries was favored relative to denaturation of an arbitrary 400-mer. This observation is consistent with the formation of secondary structure resulting from the intramolecular annealing of the perfectly complementary 21 bases at the end of each library member. These single-stranded, nonhomologously recombined DNA libraries were then available for in vitro selections.

EXAMPLE

Evolution of New DNA Receptor for cAMP

Several rounds of diversification using the shuffling method described here are used to evolve DNA receptors capable of binding cyclic AMP (cAMP) (see, e.g., FIG. 3 of U.S. Application Serial No. 60/277,015, filed on Mar. 19, 2001). Initial diversity was obtained by using the two libraries, library A and B above. Each library (100 μg for round 1 and 10 μg for subsequent rounds) of ~$10^{15}$ shuffled DNAs was dissolved in buffers containing 50 mM Tris pH 8.0, 150 mM NaCl, and varying concentrations of divalent magnesium, manganese, and zinc cations (initially 10 mM, 1 mM, and 10

µM, respectively). The library was loaded onto a column of resin-bound cAMP and washed extensively with buffer. Bound DNAs were eluted with buffer containing 1 mM free cAMP. Stringency between rounds was increased by lowering the concentration of divalent cations and increasing the speed of loading and eluting the resin (thus applying selective pressure for superior on-rate kinetics). Recovered library members were amplified by PCR with the adapter primer, digested with BciVI or EcoRI to remove the adapter, and then either cloned into pBR322 for DNA sequencing or passed on to the next round of diversification. Evolutionary pressure to specifically bind cAMP can be introduced by washing the resin-bound library members with cGMP, cIMP, AMP, and other nucleoside analogs. After two rounds of selection, a pool of enriched sequences was obtained for further analysis and selection.

EXAMPLE

Evolution of a DNA Receptor for Avidin

The method is used to evolve a DNA aptamer that can bind to avidin with high affinity and be released by biotin, thereby providing a DNA analog that can function in place of biotin.

For this example, we compared side-by-side the results of using error-prone PCR versus NRR to evolve DNA aptamers that bind streptavidin. Starting with two parental sequences of modest avidin affinity, evolution by NRR resulted in avidin aptamers with 5- to 8-fold higher affinity ($K_d$=~14 nM) than those evolved by error-prone PCR. In addition to evolving more potent function than error-prone PCR, NRR also greatly facilitates the identification of critical regions within evolved sequences. Inspection of a small number of NRR-evolved clones rapidly identified a 40-base DNA sequence that possesses streptavidin binding activity. Non-homologous random recombination (NRR) enhances the effectiveness of nucleic acid evolution and facilitates the identification of structure-activity relationships among evolved sequences.

We successfully minimized a DNA-based streptavidin binding aptamer both by inspection of NRR-evolved sequences and, independently, by controlling the size of the recombined molecules during the NRR process.

The approach of this example includes the following features. First, the approach favors intermolecular ligation. In contrast, the simple addition of DNA ligase enzymes to double-stranded, blunt-ended fragments tends to result in intramolecular circularization rather than intermolecular ligation. Second, the approach constructs defined sequences at the ends of the fragments. These defined sequences serve as primer binding sites for PCR amplification following selection. Third, the size of recombined products is controlled since sequences that are too large can be difficult to analyze or amplify, and those that are too small may not be able to fold into secondary structures with optimal desired properties.

Results. A starting pool of DNA (for example, random, genomic, or defined sequences) is digested with DNase I. The average size of the resulting fragments is controlled by varying the concentration of DNase I and the duration of the digestion. Fragments of the desired length are purified by preparative gel electrophoresis and treated with T4 DNA polymerase (which can both fill in 5' overhangs and degrade 3' overhangs) to generate blunt-ended, 5'-phosphorylated double-stranded fragments. These blunted-ended fragments are treated with T4 DNA ligase in the presence of 15% poly (ethylene glycol) (PEG). Under these conditions, intermolecular ligation is strongly favored over intramolecular circularization. Since T4 DNA ligase catalyzes the efficient ligation of blunt-ended DNA independent of sequence, fragments recombine randomly and non-homologously. In order to both control the average length of recombined molecules and to install defined sequences at the ends of the diversified DNA library, a synthetic 5'-phosphorylated hairpin is added in a defined stoichiometry to the ligation reaction. Because a DNA molecule capped by ligation to the hairpin can no longer ligate with other molecules, increasing the concentration of hairpin decreases the average length of the recombined library. The hairpin-terminated, recombined DNA pool is then digested with a restriction endonuclease that specifically cleaves at the end of the hairpin sequence to provide the recombined library of linear, double-stranded DNA molecules flanked by a single defined sequence at each end. These molecules are suitable for PCR amplification using a single primer sequence that anneals at both ends of each library member.

To test the ability of this method to recombine DNA non-homologously, we subjected several pairs of unrelated DNA sequences (~150-300 bp each) to the NRR process described above. The two parental sequences were digested to fragment sizes of 25-75 bp, and then recombined to target sizes of 200-300 bp. The average size of the recombined library could be controlled by modulating the stoichiometry of hairpin in the ligation reaction. Following PCR amplification of the recombined library, individual daughter clones were subcloned into plasmids and sequenced. At recombination junctions (crossovers), the number of bases of homology between the corresponding regions of the parental sequences was counted by inspection. The results of analyzing 124 crossovers from these experiments are as follows. An average of 0.8 bases of homology was found at each crossover, consistent with the theoretical average of 0.7 bases of homology ($2\times\Sigma 0.25^n$) expected from random chance. As expected, the most frequent crossover events took place with zero bases of sequence homology. These results indicate that NRR allows the facile nonhomologous recombination of unrelated DNA sequences in a length-controllable manner.

Comparison of Nucleic Acid Evolution by NRR Versus Error-prone PCR

To determine how nonhomologous recombination affects the efficiency of nucleic acid evolution compared with point mutagenesis, we evolved a DNA-based streptavidin aptamer using either NRR or error-prone PCR using identical selection conditions and identical starting sequences. A partially mature pool of streptavidin aptamers was generated by subjecting $5\times10^{14}$ random 200-mers to three rounds of selection and PCR amplification (SELEX) for binding to streptavidin-linked agarose and elution with free streptavidin. Following three rounds of SELEX, two arbitrarily chosen library members, S3-13 (200-mer) and S3-16 (273-mer), were sequenced and their affinities to free streptavidin were measured to be $K_d$=89±14 nM and 133±42 nM, respectively.

The sequence of S3-13 is:

```
5'-CGGGGGTGCCCGCTGCTCGTCCAAATGACGGCTCAGCTTCGGTGGGCCTTTAA      (SEQ ID NO:3)
CAGTAATCAATCATATGAGCAGTTTTCAACGATCACCTACCCACACCGCTCGAATGTTTG
CATAAACCTGGGTAGACTCACGCATAATTGGGTTATTGAGTCTCTTTGATGGACTAACCC
GGTTCTATCTCGGAGGTATTTTAGGTC-3'
```

The sequence of S3-16 is:

```
5'-TGACACAAAGACAGACAGGCTATCCAAGAACCCTCTTACTCTGTGAGACGACG      (SEQ ID NO:4)
CACCGGTCGCAGGTTTTGTCTCACAGACGCTAAAAATACAGACATGCACCAATGAACAA
TGAGTTCGACCGTGTTCTTGAGTTTTATGGCCGATGTGGTAAGTACTTCTACTGTATCTTC
GCGTACCTTAGGTTTAACGTTCTCTTTTTCGGAATGTGCTCGCCCGCGGCATCCGACGTCC
CTTTGGGGGGTAGGTGCAACGGGAATCTTGAGGGATCATT-3'
```

These two sequences share no homology. These two parental sequences were diversified using either error-prone PCR or NRR to generate three libraries. Error-prone PCR was used to generate a library of point-mutated S3-13 variants and a separate library of mutated S3-16 variants. The third library (termed 13×16) was generated by subjecting S3-13 and S3-16 to NRR using 25-75 bp fragments and recombining to a target size (250 bp) similar to the length of the parents. Following this diversification step, all three libraries were denatured into single-stranded DNA (note that the 5' and 3' ends of each library member were complementary) and subjected to three rounds of SELEX under identical conditions to enrich the sequences with the highest binding affinities. The average streptavidin affinities of the resulting three pools (designated 13E, 16E, and 13×16) were measured as well as the affinities of several individual clones from each pool.

Error-prone PCR of S3-13 followed by three rounds of enrichment yielded a pool of sequences with an average affinity for streptavidin comparable to, or slightly better than, that of S3-13 (average 13E $K_d$=68±18 nM), suggesting that point mutagenesis alone is unable to significantly improve the affinity of S3-13. Similarly, the evolution of S3-16 by error-prone PCR also resulted in only very modest increases in average binding affinity (average 16E $K_d$=111±22).

Sequences of typical clones arising from the 13E, 16E, and 13×16 libraries were determined. Error-prone PCR introduced mutations into the parental sequences at a rate of approximately 1.3% per base (27 mutations in 2,087 sequenced bases). An examination of these sequences fails to provide obvious structure-function insights such as identifying the active motif within the active sequences; indeed there are no clear correlations between the location or nature of the point mutations and the affinities of the mutant clones.

Using NRR-derived Sequences to Gain Structure-function Insights

In contrast to error-prone PCR, subjecting S3-13 and S3-16 to NRR followed by three rounds of enrichment yielded aptamers with an average streptavidin affinity of $K_d$14±5 nM. This represents a 6- to 10-fold increase in binding affinity relative to the parental sequences, and a 5- to 8-fold improvement compared with evolution by error-prone PCR. Taken together, these results indicate that, at least in this implementation, while point mutagenesis provided only very modest improvement during DNA aptamer evolution for streptavidin binding, exploring sequence space by NRR yielded significantly more potent streptavidin binders.

An analysis of sequences generated by NRR indicates that nonhomologous recombination, deletion, repetition, and reordering of sequence motifs commonly occurs during NRR. Importantly and in contrast to error-prone PCR, the comparison of even a modest number of these sequences indicates valuable structure-function relationships. Because nonhomologous recombination freely juxtaposes unrelated sequences, only the crucial regions of nucleic acids evolved by NRR are expected to be conserved. Indeed, every sequenced 13×16 clone shares a common subsequence despite their otherwise dramatic differences, and an alignment of the sequences of eight clones from the 13×16 library suggested that a 40-base DNA motif may be in part responsible for streptavidin affinity. NRR recombined sequences are exemplified by the following clones:

13×16#1:

```
5'-GAAAACTGCTCATATGATTGATTAGCCCGCTGCTCGTCCAAATGACGGCTCAG      (SEQ ID NO:5)
CTCTGTATTTTTAGCGTCTGTGAGACAGAACCTGCGACCGGTGCGTCGTCTCACAGTCTA
CTGTATCTTCGCGTACCTTAGGTTTACCCGCTGCTCGTCCAAATGACGGCTCTCTGTGAG
ACAAAACCTGCGACCGGTGCGTCGTCTCACAGTAAGAGGGTTCTTGGATA-3'
```

and 13×16#5:

```
5'-CAAGAACACGGTCGAACTCATTGTTCATTGGTGCACTGTGAGACAAAACCTGC    (SEQ ID NO:6)

GACCGGTGCGTCGTCTCACAGGAGATAGAACCGGGTTAGTCCATCAAAGAGACTCTGTG

AGACAAAACCTGCGACCGGTGCGTCGTCTCACAGAGTA-3'
```

We synthesized both complementary strands of this 40-base sequence and measured the ability of each strand to bind streptavidin. While one strand demonstrated no streptavidin affinity, the other strand with the sequence:

5'-TCTGTGAGACGACGCACCGGTCGCAG-GTTTTGTCTCACAG-3' (SEQ ID NO:7) possessed streptavidin binding affinity comparable to that of the sequences evolved by error-prone PCR despite its 5- to 7-fold smaller size relative to S3-13 or S3-16. Using Mfold for DNA (an RNA folding prediction program), this minimal streptavidin aptamer is predicted to fold into the stem-loop structure. The rapid identification of a minimal active DNA from a library evolved by NRR without requiring additional mutagenesis experiments suggests that NRR may reveal important structure-function information in addition to exploring sequence space more efficiently compared with existing methods for nucleic acid diversification.

The following table summarizes the binding constants measured for the parent nucleic acids and evolved progeny.

TABLE 1

Binding Data

| Nucleic acid | Binding constants (nM) |
|---|---|
| Parent 13 | 89 ± 14 |
| Parent 16 | 133 ± 42 |
| Diversified, then selected pools: | |
| Parent 13 EPPCR Pool | 73 ± 14 |
| Parent 16 EPPCR Pool | 104 ± 25 |
| 13 & 16 NRR Pool | 13 ± 4 |
| Individual clones: | |
| 13 EPPCR #3 | 193 ± 43 |
| 13 EPPCR #4 | 51 ± 13 |
| 13 EPPCR #5 | 116 ± 17 |
| 13 EPPCR #6 | 81 ± 22 |
| 16 EPPCR #2 | 104 ± 15 |
| 16 EPPCR #3 | 142 ± 53 |
| 16 EPPCR #4 | 65 ± 10 |
| 16 EPPCR #5 | 88 ± 6 |
| 13X16 #1 | 4.7 ± 1 |
| 13X16 #2 | 20 ± 8 |
| 13X16 #3 | 10.7 ± 0.5 |
| 13X16 #5 | 5.3 ± 2.6 |
| 13X16 #7 | 23 ± 9 |
| 13X16 #8A | 7.3 ± 3.4 |
| 13X16 #8B | 3.3 ± 1.2 |

Nucleic Acid Minimization by NRR

The ability of NRR to transform DNA fragments of defined average length into recombined clones of defined average length may allow the removal of nonessential regions from a single parental sequence to generate partially minimized clones. To test this possibility, we subjected a single high-affinity clone from the 13×16 library (13×16#8B, which is 281 nucleotides) to NRR using fragments 25 to 75 bp and a recombined target size of about 100 bp. The NRR-diversified library was subjected to three rounds of SELEX under the same conditions used to select the 13E, 16E, and 13×16 libraries. The resulting enriched library (13×6#8Bmin) demonstrated an average streptavidin binding affinity of $K_d$89±15 nM, comparable to that of the minimal 40-mer. The characterization of the three smallest individual clones isolated from this library revealed affinities consistent with the affinity of the pool ($K_d$79 to 108 nM) and lengths of 137-159 nucleotides. These results suggest that even in the absence of any sequence data, the ability of NRR to control the length of an evolving pool of nucleic acids allows the partial minimization of active sequences.

Discussion

We have developed a simple method for diversifying nucleic acids during evolution by nonhomologous random recombination. This method is an effective means of exploring sequence space. NRR not only allows multiple recombination events to take place between any DNA sequences at any position, but also allows the deletion, reordering, and repetition of motifs present in evolving nucleic acid pools. The NRR diversification method is sufficiently straightforward that transforming parental DNA into a PCR-amplified, nonhomologously recombined library could be achieved in a single day. Using NRR, DNA-based streptavidin aptamers were evolved with tight binding affinities, while, in this implementation, evolution using error-prone PCR under identical selection conditions resulted in 10-fold worse average affinities. In addition to generating molecules with greater desired properties during evolution, NRR can also more readily provide structure-function information about evolved sequences compared with error-prone PCR. A minimal 40-mer with streptavidin binding activity was isolated by simple inspection of NRR-generated sequences. NRR was also used to minimize an evolved sequence by subjecting a single active clone to NRR with a small recombined target length.

Several of the high affinity streptavidin binders generated by NRR possess multiple copies of the active 40-mer motif. Because streptavidin is a symmetric protein, it is possible that NRR-evolved sequences have taken advantage of avidity effects to simultaneously bind two or more symmetry-related epitopes of streptavidin. Because some of the highest affinity aptamers do not possess multiple copies of the active 40-mer, avidity effects alone cannot account for the significantly increased affinity of the NRR clones compared with the clones generated by error-prone PCR or the minimal 40-mer itself. The orientations of the active 40-mer relative to flanking motifs and subtle conformational differences between the NRR-evolved clones and the less active variants may also contribute to the enhanced binding of the NRR-derived sequences. Taken together, our findings suggest that nonhomologous recombination may more readily access these differences than point mutagenesis. Consistent with this hypothesis, neither the S3-16 parent nor any of the point mutated 16E clones possessed greater streptavidin affinity than the assayed 13×16 clones, despite the fact that the active 40-mer sequence was present in all of these clones.

Although the examples described here subjected either one or two parental sequences to NRR in order to trace the parentage of each resulting daughter clone, NRR can also be used to diversify a library of many different clones. Such diversification may result in even more significant improvements in desired activity. Of course, NRR can similarly be used for the evolution of RNA in addition to DNA, and for protein coding sequences.

Experimental Details

Primer oligonucleotides were synthesized by standard automated phosphoramidite coupling methods and purified by reverse-phase HPLC. Hairpin oligonucleotides and random oligonucleotides for the initial pool were purchased from Sigma Genosys (Houston, Tex.). Agarose gels were stained with ethidium bromide and visualized with UV light. DNA quantitation was performed by UV spectrophotometry and by gel electrophoresis, staining, and densitometry. Quantitation of radioactivity for binding assays was performed by phosphorimager (Molecular Dynamics), and binding curves were fit using Microsoft Excel. Restriction endonucleases, T4 DNA ligase, Vent DNA polymerase, T4 polynucleotide kinase, and T4 DNA polymerase were obtained from New England Biolabs (Beverly, Mass.). Polymerase chain reactions were performed using Taq PCR Mastermix from Promega (Milwaukee, Wis.), on a PTC-200 thermal cycler (MJ Research, Waltham, Mass.). Individual sequences were cloned using the TOPO TA cloning kit from Invitrogen (Carlsbad, Calif.).

Hairpin and primer sequences: Hairpin/primer sets were changed occasionally to avoid contamination and had no significant impact on the average streptavidin affinity of evolving pools. Contamination was monitored during each PCR reaction with a negative control reaction lacking added template DNA.

hairpin 1: 5'-phosphate-CTGTCCGGATACAAGCTTCAGCTGGGCCCGCGCGGGCCC AGCTGAAGCTTGTATCCGGACAG-3' (SEQ ID NO:8)

primer 1: 5'-CTGAAGCTTGTATCCGGACAG-3', (SEQ ID NO:9)

hairpin 2: 5'-phosphate-CCTCCGCGGCATCCGAATTCAGGCCTCCGGGCGCCCGGAG GCCTGAATTCGGATGCCGCGGAGG-3' (SEQ ID NO:10)

primer 2: 5'-CCTGAATTCGGATGCCGCGGAGG-3' (SEQ ID NO:11)

Double stranded $N_{40}$) construction: 5 nmol template (5'-GCCCCGCGGATGGGACGTCCC-$N_{40}$-CGCCCGCGGCATCCGACGTCCC-3'; SEQ ID NO:12) and 5 nmol of primer (5'-GGGACGTCGGATGCCGCGGGCG-3'; SEQ ID NO:13) were annealed and extended with Vent DNA polymerase (94° C. for 2 min 30 s, 65° C. for 30 s, add polymerase, 75° C. for 1 h). The 83 bp product was digested with Fok I to remove the ends and the resulting 40 bp product was purified by gel electrophoresis on a 3% agarose gel. The purified material was treated with T4 DNA polymerase to create blunt ends and purified by gel filtration (Centrisep columns, Princeton Separations). The 40 bp blunt-ended product was quantitated by densitometry on a 3% agarose gel.

Initial pool: 57 pmol double stranded $N_{40}$ was ligated to 57 pmol hairpin 1 under intermolecular blunt ligation conditions (15% PEG 6000, 50 μM ATP in NEB T4 DNA ligase buffer (-ATP) using 120 Weiss units of T4 DNA ligase, 25° C., 1 h.) This ratio was empirically determined to give products averaging 250 bp. The products were digested with Pvu II to remove the hairpin ends. The resulting fragments were amplified under error-prone PCR conditions in 9.6 mL (94° C. for 2 min 30 s, then cycled 40 times at 94° C. for 30 s, 60° C. for 30 s, 72° C. for 1 min 10 s). The PCR products were extracted with 1:1 phenol:chloroform and ethanol precipitated to yield a library of approximately $5\times10^{14}$ molecules with an average size of 250 bp.

Fragmentation of sequences for nonhomologous random recombination: PCR amplified products were digested with the appropriate type IIS restriction endonuclease (BciV I for primer 1 or Fok I for primer 2) to remove the primer ends. Alternatively, if the sequence of an individual clone was known, primers were synthesized to PCR amplify the sequence without the hairpin ends. The resulting fragments were digested with DNase I (Sigma), in 10 mM $MgCl_2$, 20 mM Tris-Cl pH 8.0 for 1 to 5 minutes at room temperature using approximately 2 μL of a 1:1000 dilution of DNase I. The digestions were monitored by agarose gel electrophoresis. When the size of fragments reached the desired average, the reaction was extracted with phenol-chloroform and exchanged into T4 DNA polymerase buffer by gel filtration. The fragments were blunted with T4 DNA polymerase, phenol-chloroform extracted, and purified by gel filtration. Fragments of the desired size range were purified on a 3% agarose gel and exchanged into T4 ligase buffer (see below) by gel filtration. The resulting pieces were quantitated by densitometry on a 3% agarose gel.

Ligation with hairpin: Blunt-ended pieces were ligated with hairpin 1 or hairpin 2 at a ratio empirically determined to generate the desired product length (typically this was similar to the theoretically calculated stoichiometry). For fragments of 50 bp average length, the ratio of 2:1 fragments:hairpin generated an average ligated product of 200 bp. Ligations were performed under intermolecular blunt ligation conditions (15% PEG 6000, 50 μM ATP in NEB T4 DNA ligase (-ATP) buffer with T4 DNA ligase, 25° C., 1 h) The ligations were extracted with phenol-chloroform and ethanol precipitated then digested with the appropriate restriction enzyme to remove the hairpin ends (Pvu II for hairpin 1 or Stu I for hairpin 2).

PCR amplification: Digested ligation products were amplified by PCR using Promega Mastermix and the appropriate primer (primer 1 for hairpin 1 or primer 2 for hairpin 2) at 1 μM. PCRs were initially denatured at 94° C. for 2 min 30 s, then cycled 40 times. Hairpin 1 PCRs were cycled as follows: 94° C. for 30 s, 60° C. for 30 s, 72° C. for 30 s. Hairpin 2 PCRs were cycled as follows: 94° C. for 30 s, 72° C. for 1 min 30 s. All PCRs were completed with a final 10 min extension at 72° C.

In vitro selections: For the three rounds of in vitro selection of the random library to generate clones including S3-13 and S3-16, the initial pool was denatured by heating to 95° C. in deionized water (Millipore) for 5 min and chilling suddenly on ice. Buffer was added to a final composition of 150 mM NaCl, 50 mM Tris-Cl pH 8.0, 10 mM $MgCl_2$ ("binding buffer") Streptavidin-agarose (0.5 mL of a 50% suspension, Sigma) was prepared by pre-washing with binding buffer in an HR5-5 column (Amersham-Pharmacia Biotech). The library was passed through the column followed by 50 mL of binding buffer. Desired sequences were eluted by washing the column with 0.25 mg free streptavidin (Sigma) in 0.5 mL binding buffer, followed by another 1.5 mL of binding buffer. The elution was extracted with phenol-chloroform and ethanol co-precipitated with 5 μg glycogen, and the resulting selected DNA molecules were amplified by PCR as above. For the in vitro selection of sequences starting with parents S3-13 and S3-16 (using libraries diversified by error-prone PCR or NRR), the library and streptavidin-agarose were shaken for one hour in 1 M NaCl, 50 mM Tris-Cl pH 8.0, 5 mM $MgCl_2$ ("stringent buffer") at a final concentration of 1 nM for both DNA and streptavidin. The mixture was loaded into an HR5-5 column and washed with 50 mL stringent buffer. Desired DNA molecules were eluted by shaking the washed beads with 0.125 mg free streptavidin in 0.9 mL stringent buffer at 25° C., 30 min. The elution was extracted with phenol-chloroform and ethanol precipitated with glycogen, and the resulting DNA was amplified by PCR as above.

Binding affinity assays: Affinities for streptavidin were measured using a radioactive filter binding assay. Pools or individual clones were amplified by PCR. One pmol was radiolabeled with 15 units T4 PNK and 10 μCi $\gamma$-$^{32}$P ATP (NEN) in T4 PNK buffer at 37° C., 1 h. Labeled DNA was extracted twice with phenol-chloroform and purified twice by gel filtration to remove ATP. The DNA was then denatured in water at 95° C. for 5 min together with 2 μg human genomic DNA (to block nonspecific DNA binding) per 5 fmol labeled DNA, and chilled in ice water for 5 mins. 5 fmol of labeled DNA plus 2 μg unlabeled human genomic DNA was added to varying amounts of streptavidin (0 to 1024 nM) in 50 μL of 100 mM NaCl, 50 mM Tris-Cl pH 8.0, 5 mM $MgCl_2$ ("assay buffer"), giving a final concentration of labeled DNA of 0.1 nM. The DNA and streptavidin were incubated at room temperature for 30 minutes. A multiscreen-HA 96 well nitrocellulose filter plate (Millipore), which retains protein-DNA complexes much better than free DNA, was pre-washed with 125 μL assay buffer then loaded with each assay sample. The samples were rapidly filtered on a vacuum manifold and the membranes washed twice with 250 uL of assay buffer. The membrane for each well was punched out from the plate using a stylus and the bound radioactive label quantitated by phosphorimager together with 1 fmol of unreacted probe.

EXAMPLE

Evolution of a DNA Catalyst

Figure 2:
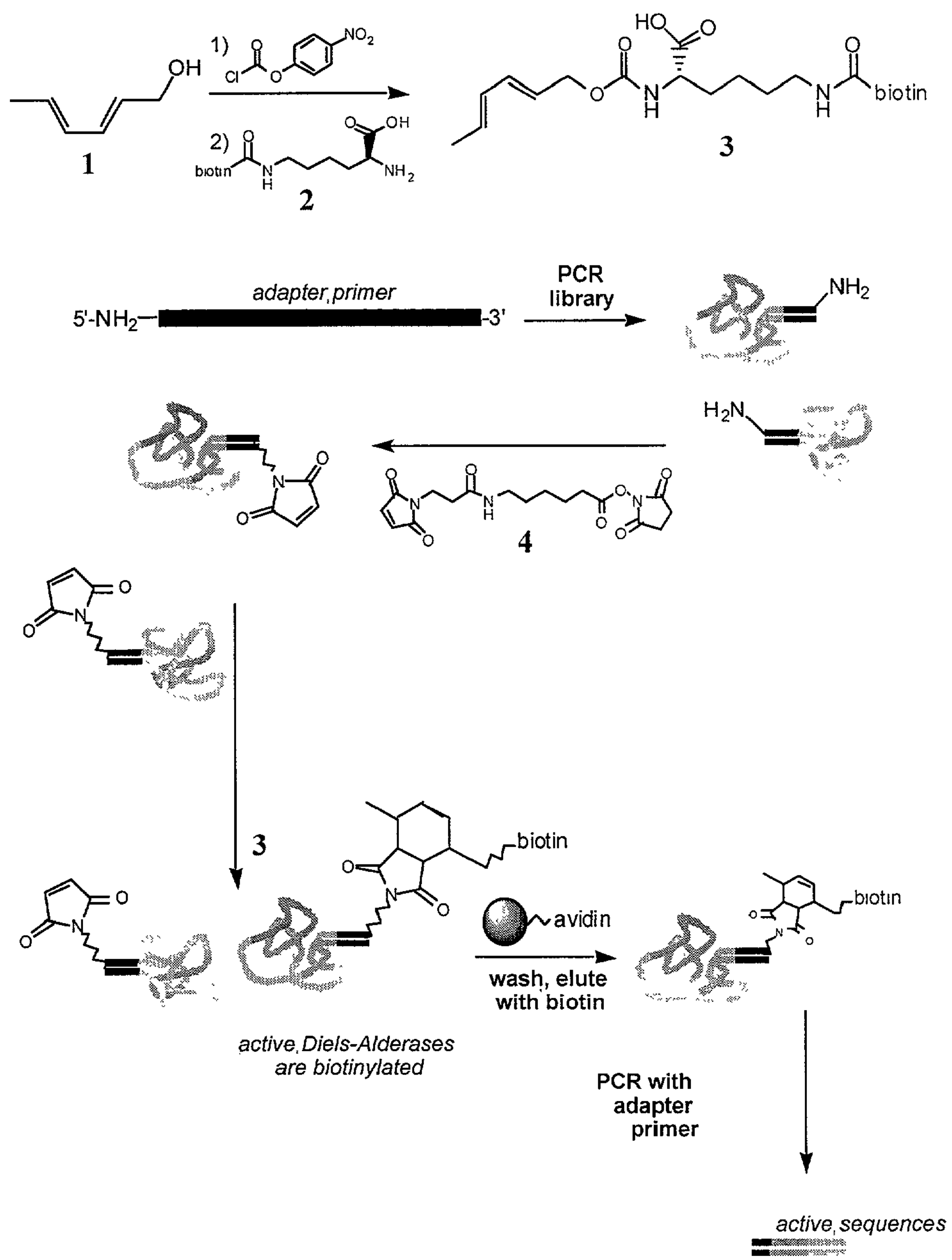
FIG. 2 is a schematic of an application of the nucleic acid shuffling method to identify nucleic acid aptamer that can catalyze the Diel-Alder reaction.

The nucleic acid shuffling method described here is used to evolve a deoxyribozyme that can catalyze the Diels-Alder cycloaddition (see FIG. 2). The method can be useful for the evolution of new catalytic nucleic acids that may be difficult to identify from a large search of sequence space. DNA possesses many desirable qualities including its chemical and biological stability, its synthetic accessibility, and its emerging suitability for multi-kilogram scale production (W. A. Wells. *Chem. Biol.* 1999, 6, R49-R5; Jaschke, Frauendorf and Hausch. *Synlett* 1999, 825-833; Famulok and Jenne. *Curr Opin Chem Biol* 1998, 2, 320-7.).

FIG. 2 depicts the selection scheme used for the evolution of a DNA Diels-Alderase (see also, e.g., Tarasow, et al. *Nature* 1997, 389, 54-57; Seelig and Jaschke. *Chem Biol.* 1999, 6, 167-76.). The p-nitrophenylcarbonate of hexadienol 1 was generated quantitatively by reaction with p-nitrophenyl chloroformate. Coupling of the carbonate to biocytin 2 generated the biotinylated diene 3 as confirmed by NMR and mass spectral analysis. DNA libraries containing 5'-amino termini were generated by PCR with 5'-amino primers and reacted with succinimidyl maleimido ester 4 to yield DNA libraries covalently linked to an electron-deficient dienophile. These libraries were incubated with the biotinylated diene 3, precipitated, and purified on resin-bound avidin to select for DNAs capable of covalently attaching themselves to biotin. Since the diene is the only potentially reactive functionality on biotin-containing 3, DNA molecules linked to biotin likely have undergone the Diels-Alder cycloaddition. The first two rounds of this selection were completed using the nucleic acid shuffling method described here to assemble and diversify the first round library followed by error-prone PCR in the second round.

Isolated nucleic acids can also be negatively selected, e.g., to remove molecules which bind to avidin, but which do not undergo the Diels-Alder cycloaddition. Additional rounds of positive selection for the Diels-Alder cycloaddition.combined with the nucleic acid shuffling method are used to isolate deoxyribozyme catalysts. Molecules isolated from each rounds can be sequenced and characterized, e.g., for kinetic parameters.

EXAMPLE

Evolution of a Polypeptide Enzyme

The nucleic acid shuffling method described here is used to evolve the TEM-1 β-lactamase of *E. coli* the enzyme that confers antibiotic resistance to ampicillin. The gene that encodes TEM-1 β-lactamase is modified to include additional unique restriction sites by the introduction of silent amino acid mutations, e.g., by mutating the wobble nucleotide of a codon. The additional restriction sites can be used for mapping or cloning recombinants. A segment of the gene that spans from the initiation codon to the termination codon (i.e., a segment which does not include an untranslated region) is isolated. The segment is treated with increasing concentrations of DnaseI for a limited time. The reaction is then terminated. Conditions that generate fragments in the range of 50 to 300 nucleotides are used. The fragments are filled in with a DNA polymerase and nucleotides. The fragments are ligated together in the presence of two hairpin oligonucleotides. The concentrations of the hairpin oligonucleotides are titrated to identify conditions that produce fragments in a desired size range, e.g., a range of 150 to 5,000 basepairs. The hairpin terminated oligonucleotides are cleaved with SmaI, amplified using primers that anneal to the hairpin in the region attached to the fragment. The amplification products are digested with a Type IIS enzyme to produce rearranged coding segments. The amplification products are cloned into a prokaryotic expression vector and transformed into an ampicillin sensitive *E. coli* strain. Transformations with ampicillin resistance are selected and identified. The shuffled bla gene in the vector can be sequenced and/or used for subsequent rounds of mutagenesis. Polypeptides encoded by the shuffled bla gene are characterized in detail, e.g., by biophysical measurements of protein stability such as by urea denaturation or thermal denaturation, and by enzymatic studies such as measurement of Michaelis-Menten coefficients, $V_{max}$, and enzymatic half-life.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising:

a) fragmenting parent nucleic acids thereby generating three or more double-stranded nucleic acid fragments that have blunt ends;

b) randomly ligating at least a subset of the blunt-ended double-stranded nucleic acid fragments to a hairpin nucleic acid and generating shuffled nucleic acids such that 5' and 3' ends of the shuffled nucleic acids are capped and can no longer ligate to other nucleic acid molecules;

c) amplifying the shuffled nucleic acids using a primer that anneals to the hairpin nucleic acid thereby generating amplified shuffled nucleic acids; and d) identifying a first selected nucleic acid for a non-coding property from the amplified shuffled nucleic acids.

2. The method of claim 1 wherein the average size of the shuffled nucleic acids is less than the size of the parent nucleic acid.

3. The method of claim 1 wherein the non-coding property is binding property of the selected nucleic acid to a ligand.

4. The method of claim 3 wherein the identifying step comprises contacting the amplified shuffled nucleic acids to a target molecule and separating the the amplified shuffled nucleic acids according to their ability to bind to the target molecule.

5. The method of claim 3 wherein the ligand comprises a polypeptide.

6. The method of claim 3 wherein the ligand comprises a small organic molecule, other than a polypeptide.

7. The method of claim 1 wherein the non-coding property is an enzymatic activity of the selected nucleic acid.

8. The method of claim 1 further comprising: identifying a second selected nucleic acid for the non-coding property from the amplified shuffled nucleic acids.

9. The method of claim 8 further comprising performing steps a) to d) by using parent nucleic acids comprising the first selected nucleic acid and the second selected nucleic acid.

10. The method of claim 8 further comprising selecting a minimal fragment from the first selected nucleic acid and the second selected nucleic acid and evaluating the minimal fragment for the non-coding property.

11. The method of claim 1 further comprising, prior to the fragmenting step, providing a plurality of nucleic acids that are degenerate oligonucleotides or are synthesized from degenerate oligonucleotides; and selecting a subset of the plurality of nucleic acids as the parental nucleic acids by evaluating a non-coding property of each of the plurality of nucleic acids.

12. The method of claim 1 wherein said fragmenting the parent nucleic acids are with a nonspecific endonuclease.

13. The method of claim 1 wherein the parental nucleic acids have a non-coding property that satisfies a criterion.

14. The method of claim 1 wherein the nucleic acid fragments are less than 5000 nucleotides and greater than 10 nucleotides in length or less than 200 nucleotides and greater than 20 nucleotides in length.

15. The method of claim 1 wherein the ligating step includes the use of T4 DNA ligase.

16. The method of claim 15 wherein the hairpin nucleic acid is DNA hairpin and is added prior to adding the DNA ligase.

17. The method of claim 1 wherein the hairpin nucleic acid is DNA hairpin and comprises 2%-25% of the molar concentration of the nucleic acid fragments.

18. A method comprising:

a) fragmenting a parent nucleic acid thereby generating three or more double-stranded nucleic acid fragments;

b) modifying the double-stranded nucleic acid fragments such that the double-stranded nucleic acid fragments have blunt ends;

c) ligating the blunt ends of at least a subset of the double-stranded nucleic acid fragments at random to a hairpin nucleic acid and generating shuffled nucleic acids such that 5' and 3' ends of the shuffled nucleic acids are capped and can no longer ligate to other nucleic acid molecules and at least one of the shuffled nucleic acids is non-homologous or in vitro non-homologous to the parent nucleic acid;

d) amplifying the shuffled nucleic acids using a primer that anneals to the hairpin nucleic acid thereby generating amplified shuffled nucleic acids; and e) identifying a first selected nucleic acid for a non-coding property from the amplified shuffled nucleic acids.

19. The method of claim 18 further comprising: identifying a second selected nucleic acid for the non-coding property from the amplified shuffled nucleic acids.

20. The method of claim 19 further comprising performing steps a) to e) by using parent nucleic acids comprising the first selected nucleic acid and the second selected nucleic acid.

21. The method of claim 19 further comprising selecting a minimal fragment from the first selected nucleic acid and the second selected nucleic acid and evaluating the minimal fragment for the non-coding property.

* * * * *

UNITED STATES PATENT AND TRADEMARK OFFICE

CERTIFICATE OF CORRECTION

PATENT NO. : 7,678,554 B2
APPLICATION NO. : 10/101461
DATED : March 16, 2010
INVENTOR(S) : David R. Liu It is certified that error appears in the above-identified patent and that said Letters Patent is hereby corrected as shown below:

Column 27, line 61 (Claim 4), please delete "the the" and insert --the-- therefor.

Signed and Sealed this

Twenty-second Day of June, 2010

David J. Kappos

*Director of the United States Patent and Trademark Office*

SEQUENCE LISTING

<160> NUMBER OF SEQ ID NOS: 13

<210> SEQ ID NO 1
<211> LENGTH: 62
<212> TYPE: DNA
<213> ORGANISM: Artificial Sequence
<220> FEATURE:
<223> OTHER INFORMATION: Syntheticaly generated oligonucleotide

<400> SEQUENCE: 1
gggaattcta gaagcttccc ggggggcccg cgcgggcccc ccgggaagct tctagaattc 60
cc 62

<210> SEQ ID NO 2
<211> LENGTH: 62
<212> TYPE: DNA
<213> ORGANISM: Artificial Sequence
<220> FEATURE:
<223> OTHER INFORMATION: Syntheticaly generated oligonucleotide

<400> SEQUENCE: 2
gggtccggat acgaattccc cgggggcccg cgcgggcccc cggggaattc gtatccggac 60
cc 62

<210> SEQ ID NO 3
<211> LENGTH: 200
<212> TYPE: DNA
<213> ORGANISM: Artificial Sequence
<220> FEATURE:
<223> OTHER INFORMATION: Aptamer

<400> SEQUENCE: 3
cgggggtgcc cgctgctcgt ccaaatgacg gctcagcttc ggtgggcctt taacagtaat 60
caatcatatg agcagttttc aacgatcacc tacccacacc gctcgaatgt ttgcataaac 120
ctgggtagac tcacgcataa ttgggttatt gagtctcttt gatggactaa cccggttcta 180
tctcggaggt attttaggtc 200

<210> SEQ ID NO 4
<211> LENGTH: 274
<212> TYPE: DNA
<213> ORGANISM: Artificial Sequence
<220> FEATURE:
<223> OTHER INFORMATION: Aptamer

<400> SEQUENCE: 4
tgacacaaag acagacaggc tatccaagaa ccctcttact ctgtgagacg acgcaccggt 60
cgcaggtttt gtctcacaga cgctaaaaat acagacatgc accaatgaac aatgagttcg 120
accgtgttct tgagttttat ggccgatgtg gtaagtactt ctactgtatc ttcgcgtacc 180
ttaggtttaa cgttctcttt ttcggaatgt gctcgcccgc ggcatccgac gtccctttgg 240
ggggtaggtg caacgggaat cttgagggat catt 274

<210> SEQ ID NO 5
<211> LENGTH: 223
<212> TYPE: DNA
<213> ORGANISM: Artificial Sequence
<220> FEATURE:
<223> OTHER INFORMATION: Exemplary motif

<400> SEQUENCE: 5

-continued

```
gaaaactgct catatgattg attagcccgc tgctcgtcca aatgacggct cagctctgta     60

tttttagcgt ctgtgagaca gaacctgcga ccggtgcgtc gtctcacagt ctactgtatc    120

ttcgcgtacc ttaggtttac ccgctgctcg tccaaatgac ggctctctgt gagacaaaac    180

ctgcgaccgg tgcgtcgtct cacagtaaga gggttcttgg ata                      223


<210> SEQ ID NO 6
<211> LENGTH: 150
<212> TYPE: DNA
<213> ORGANISM: Artificial Sequence
<220> FEATURE:
<223> OTHER INFORMATION: Exemplary motif

<400> SEQUENCE: 6

caagaacacg gtcgaactca ttgttcattg gtgcactgtg agacaaaacc tgcgaccggt     60

gcgtcgtctc acaggagata gaaccgggtt agtccatcaa agagactctg tgagacaaaa    120

cctgcgaccg gtgcgtcgtc tcacagagta                                    150


<210> SEQ ID NO 7
<211> LENGTH: 40
<212> TYPE: DNA
<213> ORGANISM: Artificial Sequence
<220> FEATURE:
<223> OTHER INFORMATION: Aptamer

<400> SEQUENCE: 7

tctgtgagac gacgcaccgg tcgcaggttt tgtctcacag                           40


<210> SEQ ID NO 8
<211> LENGTH: 62
<212> TYPE: DNA
<213> ORGANISM: Artificial Sequence
<220> FEATURE:
<223> OTHER INFORMATION: Primer

<400> SEQUENCE: 8

ctgtccggat acaagcttca gctgggcccg cgcgggccca gctgaagctt gtatccggac     60

ag                                                                    62


<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9

ctgaagcttg tatccggaca g                                               21


<210> SEQ ID NO 10
<211> LENGTH: 64
<212> TYPE: DNA
<213> ORGANISM: Artificial Sequence
<220> FEATURE:
<223> OTHER INFORMATION: Primer

<400> SEQUENCE: 10

cctccgcggc atccgaattc aggcctccgg gcgcccggag gcctgaattc ggatgccgcg     60

gagg                                                                  64


<210> SEQ ID NO 11
```

-continued

```
<211> LENGTH: 23
<212> TYPE: DNA
<213> ORGANISM: Artificial Sequence
<220> FEATURE:
<223> OTHER INFORMATION: Primer

<400> SEQUENCE: 11

cctgaattcg gatgccgcgg agg                                         23


<210> SEQ ID NO 12
<211> LENGTH: 83
<212> TYPE: DNA
<213> ORGANISM: Artificial Sequence
<220> FEATURE:
<223> OTHER INFORMATION: Template
<221> NAME/KEY: misc_feature
<222> LOCATION: 22-61
<223> OTHER INFORMATION: n = a, g, c, or t

<400> SEQUENCE: 12

gccccgcgga tgggacgtcc cnnnnnnnnn nnnnnnnnnn nnnnnnnnnn nnnnnnnnnn      60

ncgcccgcgg catccgacgt ccc                                         83


<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13

gggacgtcgg atgccgcggg cg                                          22
```